(12) United States Patent
Pedrocchi et al.

(10) Patent No.: US 11,173,091 B2
(45) Date of Patent: Nov. 16, 2021

(54) DEVICE FOR CONTROLLED ASSISTANCE OF THE GRIP

(71) Applicant: POLITECNICO DI MILANO, Milan (IT)

(72) Inventors: Alessandra Laura Giulia Pedrocchi, Milan (IT); Giovanni Maria Foglia, Milan (IT)

(73) Assignee: POLITECNICO DI MILANO, Milan (IT)

( * ) Notice: Subject to any disclaimer, the term of this patent is extended or adjusted under 35 U.S.C. 154(b) by 281 days.

(21) Appl. No.: 16/492,727

(22) PCT Filed: Mar. 13, 2018

(86) PCT No.: PCT/IB2018/051652
§ 371 (c)(1),
(2) Date: Sep. 10, 2019

(87) PCT Pub. No.: WO2018/167658
PCT Pub. Date: Sep. 20, 2018

(65) Prior Publication Data
US 2021/0137766 A1    May 13, 2021

(30) Foreign Application Priority Data
Mar. 14, 2017   (IT) .................. 102017000027918

(51) Int. Cl.
*A61H 1/02* (2006.01)
*A61F 4/00* (2006.01)

(52) U.S. Cl.
CPC ... *A61H 1/0285* (2013.01); *A61H 2201/0153* (2013.01); *A61H 2201/1207* (2013.01);
(Continued)

(58) Field of Classification Search
CPC ............ A63B 21/00192; A63B 21/115; A63B 21/4021; A41D 19/01547; H01F 7/206
(Continued)

(56) References Cited

U.S. PATENT DOCUMENTS 5,516,249 A    5/1996   Brimhall
5,715,539 A *  2/1998   Benecki ........... A41D 19/01564
                                                        2/160
(Continued)

FOREIGN PATENT DOCUMENTS

WO   2015/004643 A2   1/2015
WO   2016/088071 A1   6/2016

OTHER PUBLICATIONS

International Search Report and Written Opinion dated Jun. 11, 2018 in corresponding International Application No. PCT/IB2018/051652; 7 pages.

*Primary Examiner* — Bradley H Philips
*Assistant Examiner* — Savannah L Gabriel
(74) *Attorney, Agent, or Firm* — Maier & Maier, PLLC

(57) ABSTRACT

A device for the controlled assistance of the grip, including a first element, which can be worn on one hand, and which includes a pair of ferromagnetic plates. The device also includes a second element which includes a ferromagnetic core whose opposite poles are each connected to one of the two ferromagnetic plates. The device further includes a power supply unit connected to an excitation coil wound around the ferromagnetic core. A control unit controls the voltage supplied by the power supply unit to the ends of the coil, so as to adjust the magnetic field generated to the ferromagnetic plates.

18 Claims, 4 Drawing Sheets

(52) U.S. Cl.
CPC ............... *A61H 2201/165* (2013.01); *A61H 2201/1638* (2013.01); *A61H 2201/501* (2013.01)

(58) Field of Classification Search
USPC ........................................... 2/161.6
See application file for complete search history.

(56) References Cited

U.S. PATENT DOCUMENTS

| | | | |
|---|---|---|---|
| 5,720,046 A * | 2/1998 | Lopez | A42B 1/24 |
| | | | 2/159 |
| 2013/0090581 A1 * | 4/2013 | Yamazaki | A41D 19/0024 |
| | | | 601/81 |
| 2018/0206563 A1 * | 7/2018 | Sandhu | A41F 1/06 |

* cited by examiner

DEVICE FOR CONTROLLED ASSISTANCE OF THE GRIP

FIELD

The present invention relates to the field of magnetic gripping devices.

The invention finds its preferred application in subjects suffering from neuromotor disability of the hand, whereby the person needs assistance to grasp and lift objects. However, the invention is not limited to this application and can also be applied in other fields, such as sports, where there is a need to assist in a variable way the manual grip capacity of a person.

In particular, the invention relates to a device according to the preamble of claim 1.

BACKGROUND

Nowadays there are several devices to improve the gripping ability of people who have lost the full or partial functionality thereof, such as multiple sclerosis patients, or those who have suffered a stroke.

Patterson Medical Holdings, Inc. manufactures telescopic rods at one end of which are pliers that can be operated by a simple mechanism, such as a trigger, located at the other end. This allows people with little force in the arm, or even without a hand, to grasp and hold objects firmly. This solution, however, is cumbersome and not suitable for rehabilitation of the hand.

The North Coast Medical Inc. company, on the other hand, produces wristbands with the Norco™ brand, which can support the wrist and have a magnetic band that crosses the palm of the hand. The magnet placed in the band allows to hold metal objects such as cutlery.

However, this solution also has some limitations, first of all the fact that it is not possible to regulate the strength of the magnet, therefore it is not possible to use this device to assist the patient in a rehabilitation process, encouraging him to increase the force used to grasp an object. Moreover, this device is based on a constant magnetic action, which cannot be disabled by the user.

Some patent solutions have provided gloves with permanent magnets able to assist the grip. These solutions do not allow the activation/deactivation and modulation of the assistance level provided by the magnet system and, being based on gloves, create a complete filter between the object and the hand, limiting the direct tactile perception of the subject.

Other known solutions provide for the use of exoskeletons, but even these have the limit of being very complex, cumbersome and expensive.

The need is therefore felt for a device to assist in a controlled manner the gripping of a subject.

SUMMARY

The object of the present invention therefore is to provide a device for the controlled assistance of the grip which solves the drawbacks of the prior art.

In particular, the object of the present invention is to implement a device that is easy to use and of simple construction.

These and other objects of the present invention are achieved by a device incorporating the features of the appended claims, which form an integral part of the present disclosure.

In one embodiment, the device for the controlled assistance of the grip of a hand comprises a first element, wearable on the hand, on the palm where possible while on the back if the subject requested it, comprising a pair of ferromagnetic plates, preferably aligned through an appropriate structure. The device then comprises a second element, electrically connected to the first element. This second element is preferably wearable on a person's wrist or arm or forearm, and comprises a ferromagnetic core whose opposite poles are each connected to one of the two ferromagnetic plates. This part could be fixed to the mechanical elements of an arm orthosis or exoskeleton, if the subject uses it.

The device further comprises a power supply unit connected to an excitation coil wound around the ferromagnetic core. A control unit controls the voltage supplied by the power supply unit to the ends of the coil, so as to adjust the magnetic field generated to the ferromagnetic plates, for example by activating it, deactivating it and also changing the level of assistance provided.

Ferromagnetic core, coil and power supply unit thus constitute an electromagnet whose magnetic field can be controlled by the control unit. This therefore allows to assist in a controlled manner the hand in the grip of any metallic ferromagnetic object (or any object to which a special ferromagnetic contribution has been added), which is very important and useful in various applications, from rehabilitative recovery therapies of the hand functionality to the daily life of subjects suffering from functional disability of the grip, up to sports applications, such as training sessions in which it is necessary to control the grip of the hand.

Advantageously, the ferromagnetic core comprises a strand of wires made of ferromagnetic material, which allows obtaining the necessary volume of ferromagnetic material without renouncing the flexibility necessary to wrap it around the wrist or arm.

In one embodiment, the ferromagnetic core and the coil form a self-winding spiral-shaped bracelet around the wrist. This allows a simple implementation of the device.

In an alternative embodiment, the ferromagnetic core and the excitation coil are arranged inside a band, preferably made of fabric, which comprises closure means, in particular Velcro or buttons, at opposite ends. An easily wearable bracelet is thus obtained.

In another embodiment, the ferromagnetic core and the excitation coil can be inserted into a pocket or bag. Advantageously, then, the device also comprises an interface operatively connected to the control unit. The control unit is configured to control the intensity of the magnetic field generated at the ferromagnetic plates in response to user commands received through the interface. This allows, therefore, an operator or the subject who wears the system to interact with the device to adjust the intensity of the magnetic field and, therefore, the assistance to the grip. In addition to determining the level of assistance, the interface allows the person to activate or deactivate the assistance of the device, ensuring the attachment of the object and its release.

The invention is not limited only to the device, but also relates to a system for the controlled assistance of the grip of a hand comprising a hand grip assistance device of the type indicated above and better described below, and a user terminal. The device for the assistance of the grip comprises a transceiver capable of receiving radio signals from the user terminal. The transceiver is operatively connected to the control unit for transmitting control signals received from the mobile terminal to the control unit, while the control unit is configured to control the power supply unit in response to the control signals received from the user terminal.

The system can also comprise ferromagnetic elements, in particular bars, provided with suitable fixing means (e.g. adhesive, Velcro, etc.) for connecting to commonly used objects, such that such objects can be effectively interfaced with the grip assistance device.

The invention is also directed to an exoskeleton incorporating the device for the controlled assistance of the grip of a hand.

Further features and objects of the present invention will become more apparent from the following description.

BRIEF DESCRIPTION OF THE DRAWINGS

The invention will be described below with reference to some examples, provided for explanatory and non-limiting purposes, and illustrated in the accompanying drawings. These drawings illustrate different aspects and embodiments of the present invention and, where appropriate, similar structures, components, materials and/or elements in different figures are indicated by similar reference numbers.

DETAILED DESCRIPTION OF THE EMBODIMENTS

Figure 1:
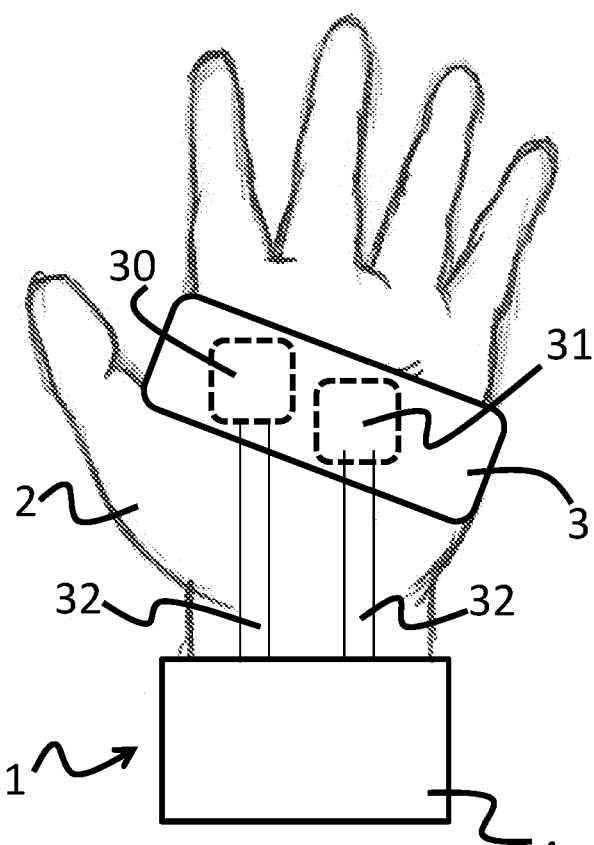
FIG. 1 shows a device for the controlled assistance of the grip of a hand according to an embodiment of the present invention.

While the invention is susceptible of various modifications and alternative constructions, some preferred embodiments are shown in the drawings and will be described in detail below. It must be understood, however, that there is no intention to limit the invention to the specific embodiment illustrated, but, on the contrary, the invention intends to cover all modifications, alternative constructions, and equivalents that fall within the scope of the invention as defined in the claims.

Use of "e.g.", "etc.", "or" means non-exclusive alternatives without limitation unless otherwise indicated. The use of "includes" means "include, but not limited to" unless otherwise indicated.

FIG. 1 shows a device, indicated as a whole with reference number 1, for the assisted control of the grip of a hand 2.

The device 1 comprises a first element 3 which can be worn on the palm of the hand 2 and a second element 4 which can be worn on the wrist.

In one embodiment, the first element 3 is an annular band of fabric that surrounds the hand, so that it can be easily worn by inserting index, middle, ring and little fingers inside the band ring leaving outside the thumb.

Alternatively, the first element 3 can comprise a C-shaped rigid bar which can be worn on the hand by inserting the part of the hand between the thumb and the index inside the concavity of the folded bar.

In subjects that cannot open their hand, the C-shaped frame can be worn on the back rather than on the palm.

In general, the first element 3 is an element wearable on the palm or on the back of the hand which comprises a pair of ferromagnetic plates 30 and 31.

The shape of the element 3 can be any, such as a glove, although preferably the first element 3 is selected as small as possible in such a way as to leave most of the palm and the hand free, so as not to limit the direct tactile interaction of the person with the object, where the pathology does not affect the skin perception.

For example, the first element 3 may be a band of fabric or a rigid bar whose width is substantially equal to the size of the ferromagnetic plates 30 and 31.

Figure 2:
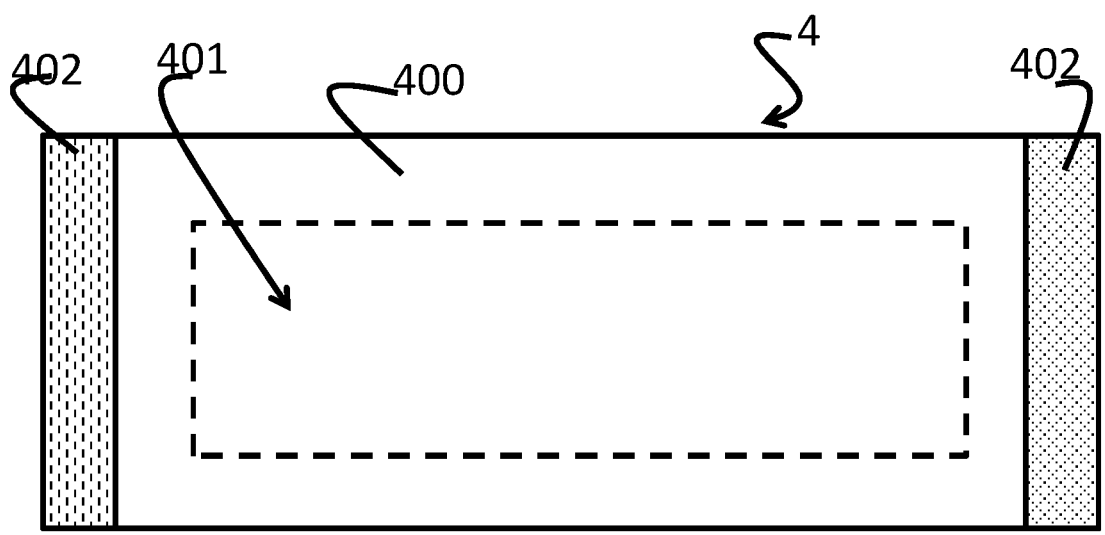
FIG. 2 shows a detail of the device of FIG. 1.
Figure 3:
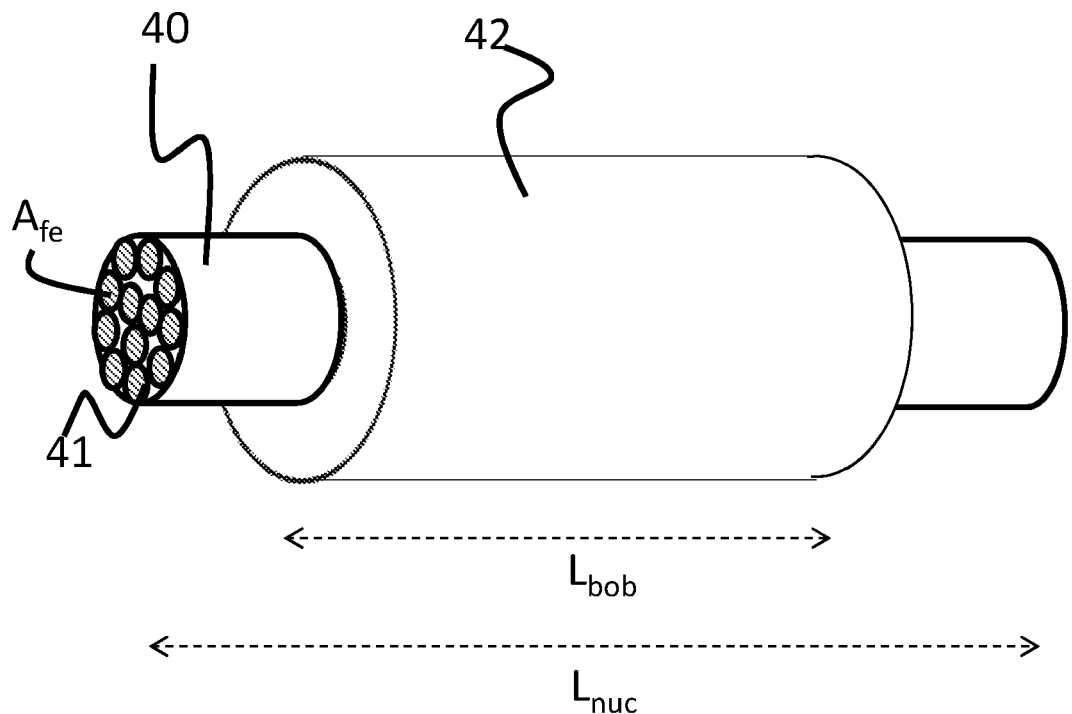
FIG. 3 shows a part of an electromagnet part of the device of FIG. 1.

The ferromagnetic plates 30 and 31 correspond to the terminations (i.e. to the opposite magnetic poles) of a ferromagnetic core 40, visible in FIGS. 2 and 3, inserted in the second element 4. The connection between the ferromagnetic plates 30 and 31 placed in the first element and the rest of the ferromagnetic core placed in the second element is made by two connections 32 which in FIG. 1 pass over the palm of the hand, but which in a preferred embodiment slide on the back of the hand.

In the example in FIG. 1, the second element 4 is a bracelet, illustrated in detail in FIG. 2, comprising a band of fabric 400 provided with a pocket 401 for housing the components of an electromagnet, which will be discussed further on. The band is closed around the arm by means of suitable closure means 402 which in the example in FIG. 2 consist of two Velcro strips. It is however possible to use other closure means, such as buttons, laces, hooks or other.

Figure 4:
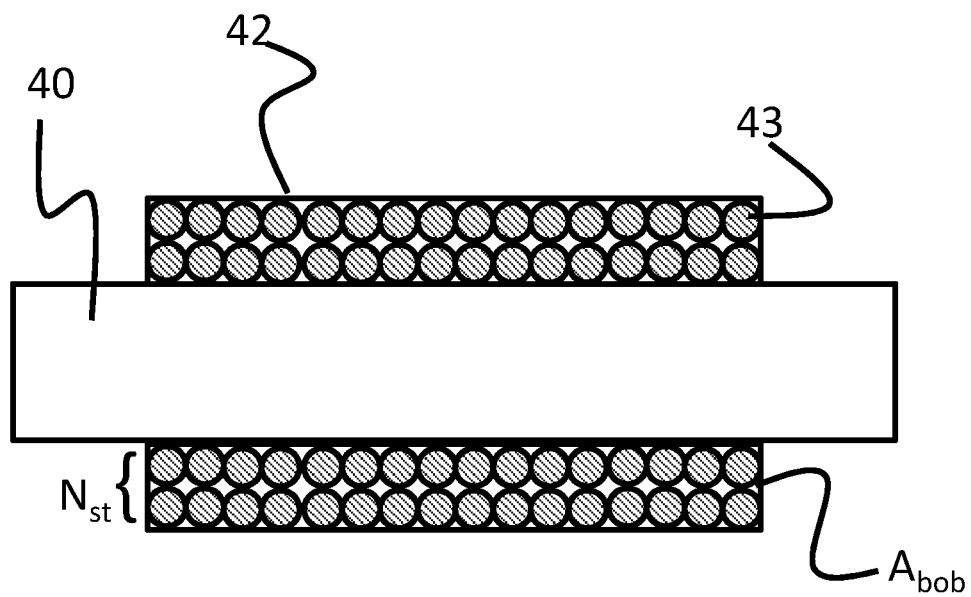
FIG. 4 shows a sectional view of FIG. 2.

In the preferred embodiment illustrated in FIGS. 3 and 4, the electromagnet comprises a ferromagnetic core 40 consisting of a strand of interlaced cables 41 made of ferromagnetic material, e.g. iron or alloys comprising iron, such as Fe—Si or Fe—Ni—Mo. This allows to obtain a core with the necessary flexibility to allow the bending thereof necessary for the bracelet 4 to be worn on a wrist.

Around the core 40 a coil 42 is wrapped, consisting of electrical conductors 43, e.g. of copper or aluminum, to which a variable voltage is applied in order to generate a magnetic field through the ferromagnetic core 40 and in particular to the plates 30 and 31 placed on the first element 3 and connected to the ferromagnetic core 40, of which they constitute the two magnetic poles.

Figure 5:
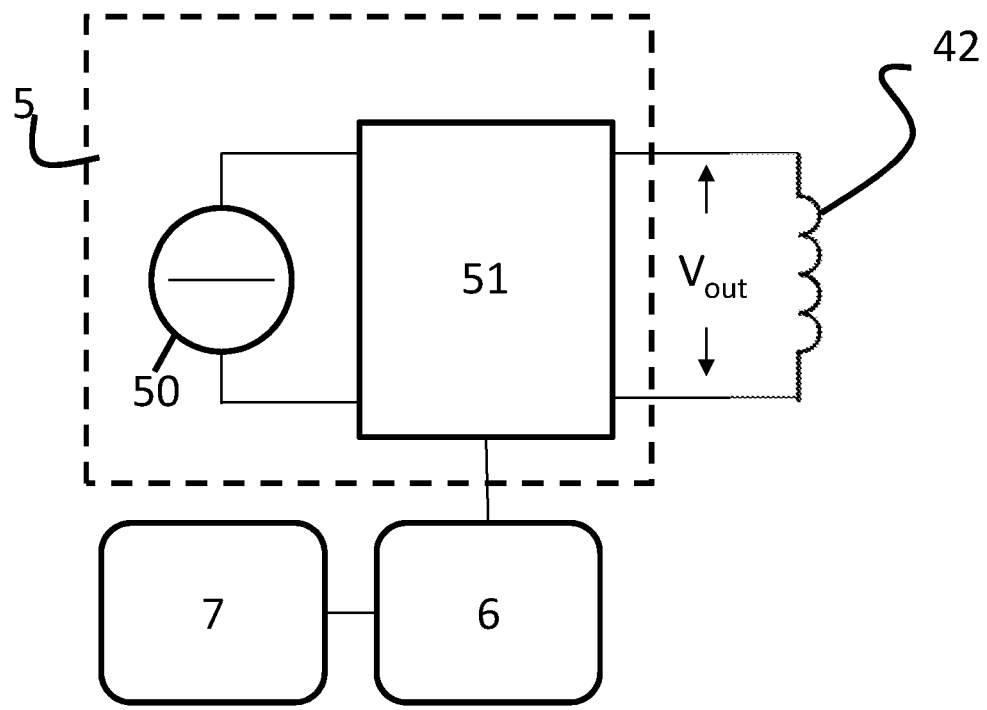
FIG. 5 shows a circuit diagram of the device of FIG. 1.

In order to generate the necessary supply voltage of the coil 42, the device 1 is provided with a power supply unit 5, visible in the electric diagram in FIG. 5, capable of generating a variable voltage $V_{out}$. To this end, in the example in FIG. 5, the power supply unit 5 comprises a direct voltage generator 50 and a converter 51 able to vary the voltage supplied by the generator 50 and, consequently, the intensity of the magnetic field generated by the plates 30 and 31. By adjusting the intensity of the magnetic field, the device 1 will be able to attract metal elements with more or less force, and therefore to assist in an adjustable manner the hand in the grip of ferromagnetic objects or provided with ferromagnetic elements (e.g. ferromagnetic strips or bars placed with suitable fixing means, such as an adhesive or Velcro on common non-ferromagnetic objects).

A control unit 6 controls the converter 51 to adjust the voltage $V_{out}$ in response to user commands that are received through an interface 7 or according to predetermined programs loaded into a memory area of the control unit 6.

Figure 6:
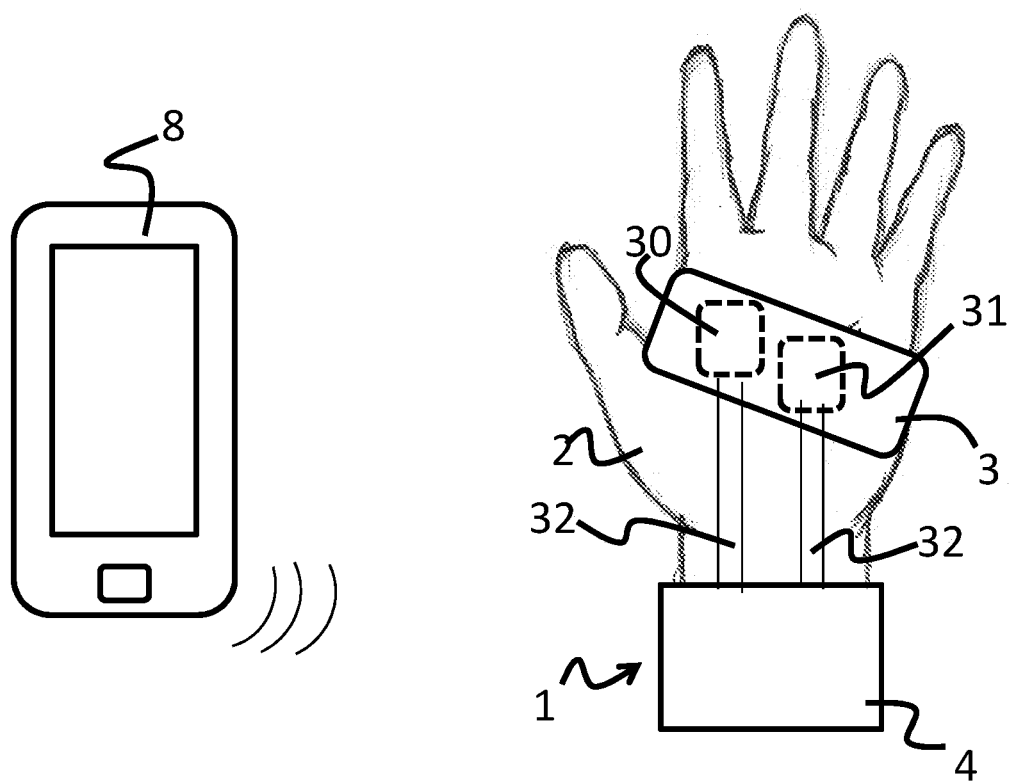
FIG. 6 shows a hand rehabilitation system comprising the device of FIG. 1.
Figure 6:
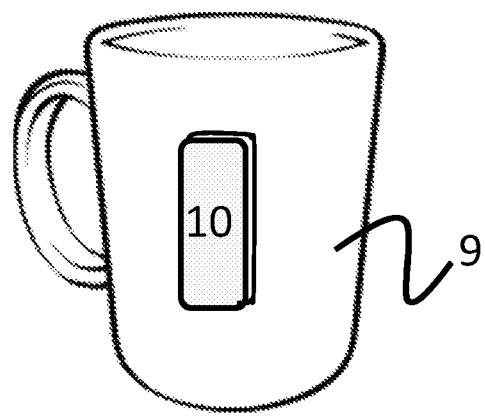

In an embodiment, illustrated in FIG. 6, the interface 7 comprises a radio receiver, e.g. a Bluetooth or Wi-Fi receiver, capable of receiving commands transmitted from a user terminal 8, such as a smartphone or a tablet or a computer. This solution allows an operator to regulate the assistance that the device 1 must give to the grip in a very simple way by acting on a device external to the device 1 and, therefore, not cumbersome. For example, in a rehabilitative therapy, it is possible to place on a common object, such as a cup 9, a ferromagnetic band 10 which can be attracted by the electromagnet when activated. The operator can act on the user terminal 8, for example through a software application, to control the device 1 in such a way that the magnetic field is initially maximum, so as to maximize the force of the magnetic field generated by the plates 30 and 31, to then reduce the intensity of the magnetic field over time and, therefore, the assistance in gripping the object 9. In other situations, where the device is used to assist patients with degenerative diseases, the operator can act on the user terminal 8 to control the strength of the magnetic field increasing it upon the degeneration of the disease.

In general, the interface 7 can be provided with a transceiver for communicating with user terminals or other external devices. For example, in a very basic solution (suitable for example for subjects with difficulty in the precise positioning of the finger on a touch screen), the external device that sends commands to the interface 7 can be a simple remote control, with a few buttons, such as only 3 buttons: an activation-deactivation one, two for voltage regulation. Alternatively, however, the interface 7 can be connected by cable to user terminals or other external devices. In general, therefore, the device 1 can be equipped with a data transfer system capable of receiving signals from user terminals or other external devices.

In light of the above it is clear how the device 1 allows to achieve the prefixed objects allowing controlled assistance of the grip.

It is also clear that the embodiments described above do not have to be intended in a limiting sense, whereas the scope of protection of the invention is instead defined by the appended claims. Many variations are therefore possible. In one embodiment, the device for the controlled assistance of the grip of a hand may be part of an exoskeleton or an orthosis. The exoskeleton or the orthesis will therefore comprise a mechanical structure (and possibly also an electrical structure) which, in a known manner, can be worn by a user to enhance the capacities thereof, for example to help him move an arm where the user has suffered injury to the arm. In this embodiment, however, the exoskeleton (or orthosis) will comprise, in the end worn on the arm, a device as herein described and claimed.

As stated above, many variations of the device are possible with respect to the preferred examples described above. For example, other circuit solutions for controlling the magnitude of the magnetic field generated by the electromagnet are possible, for example, the interface 7 could comprise a touch screen, through which the operator can provide commands to the device 1 and optionally control the operating parameters thereof. Furthermore, the power supply unit could at most consist of a voltage generator and a switch that can be operated to connect and disconnect the voltage generator to the coil.

In a preferred embodiment, the power supply unit 5 is mounted on the second element 4, for example it has compact dimensions which allow it to be housed in a pocket of the bracelet 4. This is, for example, possible using a battery of the type used for smartphones as a generator 50 and using an integrated circuit comprising the necessary control logic for implementing the converter 51, the control unit 6 and the interface 7.

Alternatively, the power supply unit can be separated from the second element and connected to the latter by suitable cables and connectors. In this embodiment, the voltage converter and/or the control unit can be indifferently placed on the bracelet wound on the wrist or be external thereto.

In one embodiment, then, the first element 3, which is worn on the hand, is shaped in such a way that the ferromagnetic plates 30, 31 are mounted on the back of the hand. In this configuration, the advantage of the direct sensorial interaction offered by the grip and the possible partial assistance in case of a weak but still partially functional subject is lost, but the possibility to grip the objects is nevertheless obtained. This alternative may be necessary if the pathology does not allow the person to open the hand, but the hand is in a closed postural attitude (in a first or pinch) due to spasticity, joint limitations, tendon retractions or other factors related to the pathology. A similar configuration may be necessary if the subject is unable to guarantee an effective opening of the hand and therefore risks that the fingers interfere with the gripping attitude. Advantageously, if the ferromagnetic plates 30, 31 are positioned on the side of the back of the hand, the connections 32 are passed over the palm of the hand. Preferably, in fact, the connections 32 are positioned so as not to occupy the side of the hand on which the ferromagnetic plates 30, 31 are positioned.

Figure 7:
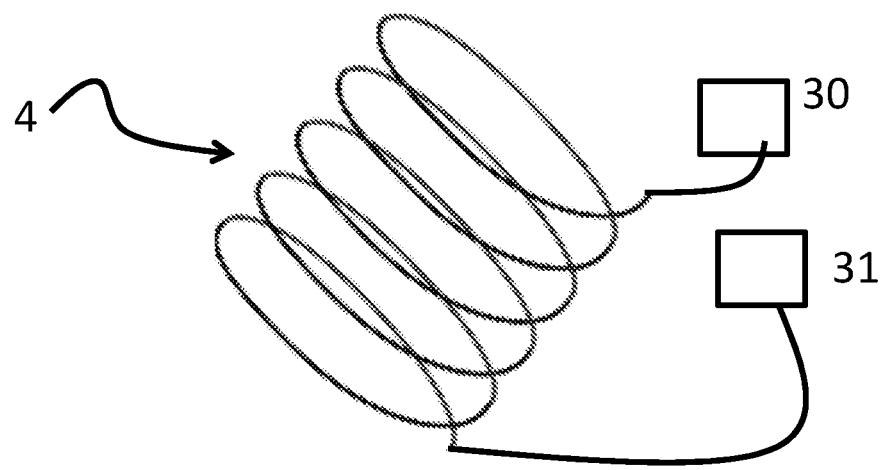
FIG. 7 shows an alternative embodiment of the electromagnet used in the device of FIG. 1.

Furthermore, in order to be able to wear the second element 4 on the wrist it is not strictly necessary for the electromagnet to be inserted into a pocket of a fabric bracelet. The electromagnet could, in fact, have a sufficient rigidity to allow it to be folded in a spiral, as shown in FIG. 7, to be able to wear it.

As far as the sizing of the device is concerned, it is clear that the number of turns and the section of the coil cables, as well as the number of cables that make up the strand of the ferromagnetic core can be chosen differently depending on the application of the device and of the magnetic field strength to be generated with the electromagnet.

Below is an example of a preferred sizing of the device 1.

Assuming that one has to lift a weight equal to 1 kg, the force to be developed is about 10 N (1 kg=9.8 N).

Considering a magnetic circuit with work induction equal to B=0.5 T, the magnetic pressure is around 10N/cm² ($p=B^2/(2*\mu_0)=0.5^2/(2*4*\Pi*10^{-7})=99470$ N/m²=9.95 N/cm²).

Therefore, two ferromagnetic plates 30, 31 would be sufficient, each having an area equal to 0.5 cm². This would also be $A_{nuc}$ section of the ferromagnetic core that generates the field, and which is connected to the plates 30 and 31.

Assuming an air gap of 1 mm between each magnetic plate and the object to be lifted, the total air gap of the circuit is 2 mm.

To produce an induction B=0.5 T with an air gap g=2 mm we need a magneto-motive force $M=g*B/\mu_0=0.002*0.5/(4*\Pi*10^{-7})=796$ A. Assuming the typical value of current density (J=4 A/mm²), a coil of total section $A_{bob}=M/J=796/4=199$ mm²≈200 mm² is required.

Considering a copper conductor of section $A_{cond}=0.1$ mm², $N_{sp}=A_{bob}/A_{cond}=200/0.1=2000$ turns are required.

The dimension Ing of the strand is a little higher than the diameter D (it must be taken into account that the electrical conductors are insulated): we assume Ing=1.4*D=1.4*radq $[A_{cond}*4/\Pi]=0.4$ mm.

The overall dimensions $IngN_{sp}$ of the $N_{sp}$ coils can be estimated as $IngN_{sp}=Ing*N_{sp}=0.4*2000=800$ mm.

Assuming to make $N_{st}=5$ layers of turns, the linear dimensions are IngLin=IngNsp/Nst=800/5=160 mm.

This is therefore the minimum length $L_{nuc}$ of the ferromagnetic core. Preferably, the ferromagnetic core is selected with a length greater than the minimum, in particular it is preferable to increase it by 20-25%, thus obtaining a length equal to $L_{nuc}$=200 mm. The so obtained ferromagnetic core is rolled into a bracelet around the wrist or forearm, causing a space of a few cm. In summary, a possible sizing of a bracelet for the assistance of the manual grip of an object up to a maximum weight of 1 kg involves the use of a ferromagnetic core of section $A_{nuc}$=0.5 cm², and length $L_{nuc}$=20 cm, which could be wrapped (like a bracelet) around the arm near the wrist, or around the forearm, requiring 2-3 turns, and then causing a footprint of a few cm. Around the core $N_{sp}$=2000 turns of a conductor of section $A_{cond}$=0.1 mm², with 5 layers of turns are wound.

The "bracelet" thus obtained is then "extended" to reach the ferromagnetic plates 30, 31 placed on the palm of the hand. To ensure a certain flexibility of these extensions, they should be made with a strand of ferromagnetic threads. With these characteristics, the current in the conductor would be $I_{cond}$=J*$A_{cond}$=4*0.1=0.4 A.

The diameter $D_{sp}$ of the average coil of the conductor would be slightly higher than the outer diameter of the ferromagnetic core $D_{nuc}$=radq[$A_{nuc}$*4/Π]=8 mm.

Let's assume $D_{sp}$=10 mm.

The length of the average coil is $L_{sp}$=Π*$D_{sp}$=31.4 mm.

Assuming to use a copper conductor and assuming to operate at a temperature of 30° C., the resistivity is ρ=0.0177*10⁻⁶.

The coil resistance is $R_{bob}$=ρ*$N_{sp}$*$L_{sp}$/$A_{cond}$=11Ω.

The required voltage is $V_{bob}$=$R_{bob}$*$I_{cond}$=11*0.4=4.4 V.

The required power is Pel=$V_{bob}$*$I_{cond}$=4.4*0.4=1.76 W.

The masses of the ferromagnetic core and of the coil are obtained by evaluating the volume and multiplying by the density. In detail, the core volume is $A_{nuc}$*($L_{nuc}$+0.3); $L_{nuc}$ is increased by 30 cm, to take into account the "extensions" that the ferromagnetic plates 30, 31 must reach. The coil volume is $A_{bob}$*$L_{sp}$, while the iron and copper densities are 7650 and 9800 kg/m³. The core and coil masses are therefore approximately 180 g and 50 g respectively.

The invention claimed is:

1. A device for the controlled assistance of the grip, comprising:
   a first element wearable on a hand; and
   a second element (4) electrically connected to the first element
   wherein
   the second element comprises
      a ferromagnetic core whose opposite poles are connected to a pair of ferromagnetic plates inserted in the first element, and
      an excitation coil comprising electrical conductors wrapped around said core, and the device further comprises
   a power supply unit connected to said excitation coil that provides a supply voltage at the terminals of the excitation coil; and
   a control unit adapted to control the supply voltage delivered by said power supply unit.

2. The device according to claim 1, wherein said ferromagnetic core comprises a strand of wires of ferromagnetic material.

3. The device according to claim 1, wherein the ferromagnetic core and the coil form a spiral-shaped bracelet that is wrapped around a part of an arm.

4. The device according to claim 1, wherein the ferromagnetic core and the coil are arranged within a band which comprises closure means at the opposite ends.

5. The device according to claim 1, wherein said second element includes means for holding said power supply unit and said control unit.

6. The device according to claim 5, wherein said second element is a bracelet which comprises a band made of fabric, that is wrapped around a wrist and comprising at least one seat for housing the ferromagnetic core, the excitation coil and the power supply unit.

7. The device according to claim 6, wherein said ferromagnetic core comprises a strand of wires of ferromagnetic material.

8. The device according to claim 6, wherein the ferromagnetic core and the coil form a spiral-shaped bracelet that can be wrapped around a part of an arm.

9. The device according to claim 6, wherein the ferromagnetic core and the coil are arranged within a band which comprises one of Velcro or buttons, at the opposite ends.

10. The device according to claim 1, further comprising an interface operatively connected to the control unit, wherein the control unit is configured to turn on/off and control the intensity of the magnetic field generated at the plates in response to user commands received through said interface.

11. The device according to claim 1, wherein when the first element is worn on the hand, said pair of ferromagnetic plates are positioned in correspondence with the palm of the hand.

12. The device according to claim 1, wherein when the first element is worn on the hand, said pair of ferromagnetic plates are positioned in correspondence of the back of the hand.

13. The device according to claim 1, further comprising an exoskeleton.

14. A System for the controlled assistance of a hand grip, comprising:
   a user terminal and a device for the controlled assistance of the grip,
   wherein the device for the controlled assistance of the grip comprises
      a first element wearable on a hand,
      a second element electrically connected to the first element, wherein the second element comprises
         a ferromagnetic core whose opposite poles are connected to a pair of ferromagnetic plates inserted in the first element, and
         an excitation coil comprising electrical conductors wrapped around said core,
      a power supply unit connected to said excitation coil for providing a supply voltage at the terminals of the excitation coil,
      a control unit adapted to control the supply voltage delivered by said power supply unit, and
      a data transfer system, capable of receiving signals from said user terminal,
   wherein said data transfer system is operatively connected to said control unit for transmitting to said control unit control signals received from said user terminal,
   and wherein said control unit is configured to control the power supply unit in response to control signals received from the user terminal.

15. The system according to claim 14, further comprising at least a ferromagnetic strip provided with suitable fastening element of one of adhesive or Velcro, adapted for connection to an object.

16. The system according to claim 14, wherein said ferromagnetic core comprises a strand of wires of ferromagnetic material.

17. The system according to claim 14, wherein the ferromagnetic core and the coil form a spiral-shaped bracelet that can be wrapped around a part of an arm, in particular the wrist.

18. The system according to claim 14, wherein the ferromagnetic core and the coil are arranged within a band which comprises closure means, comprising one of Velcro or buttons, at the opposite ends.

* * * * *